United States Patent
Ries et al.

(10) Patent No.: US 8,996,113 B2
(45) Date of Patent: Mar. 31, 2015

(54) RECOMMENDED REPLACEMENT TIME BASED ON USER SELECTION

(75) Inventors: Andrew J. Ries, Lino Lakes, MN (US); Craig L. Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 13/308,198

(22) Filed: Nov. 30, 2011

(65) Prior Publication Data

US 2013/0138166 A1  May 30, 2013

(51) Int. Cl.
 A61N 1/378 (2006.01)
 A61N 1/37 (2006.01)
 A61N 1/39 (2006.01)

(52) U.S. Cl.
 CPC ............ *A61N 1/3708* (2013.01); *A61N 1/3975* (2013.01); *A61N 1/3937* (2013.01)
 USPC .................................................. 607/29; 607/7

(58) Field of Classification Search
 CPC ..... A61N 1/08; A61N 1/3706; A61N 1/3708; A61N 1/378; A61N 1/3925; A61N 1/3937; A61N 1/3975
 USPC ..................... 607/7, 11, 16, 27, 29, 30, 34, 59
 See application file for complete search history.

(56) References Cited

U.S. PATENT DOCUMENTS

| | | | |
|---|---|---|---|
| 4,259,639 A | 3/1981 | Renirie | |
| 4,448,197 A * | 5/1984 | Nappholz et al. | 607/29 |
| 5,193,538 A * | 3/1993 | Ekwall | 607/29 |
| 5,370,668 A | 12/1994 | Shelton et al. | |
| 5,620,474 A * | 4/1997 | Koopman | 607/29 |
| 5,741,307 A * | 4/1998 | Kroll | 607/5 |
| 5,925,068 A | 7/1999 | Kroll | |
| 6,016,448 A * | 1/2000 | Busacker et al. | 607/29 |
| 6,108,579 A * | 8/2000 | Snell et al. | 607/29 |
| 6,154,675 A * | 11/2000 | Juran et al. | 607/29 |
| 6,185,461 B1 * | 2/2001 | Er | 607/27 |
| 6,247,474 B1 * | 6/2001 | Greeninger et al. | 128/899 |
| 7,001,359 B2 * | 2/2006 | Rogers | 604/118 |
| 7,142,923 B2 * | 11/2006 | North et al. | 607/30 |
| 7,194,308 B2 | 3/2007 | Krig et al. | |
| 7,769,455 B2 | 8/2010 | Armstrong et al. | |
| 7,818,060 B2 | 10/2010 | Torgerson | |
| 7,912,546 B2 | 3/2011 | Eriksson | |
| 2004/0162592 A1 * | 8/2004 | Betzold et al. | 607/27 |
| 2005/0007073 A1 | 1/2005 | James et al. | |

* cited by examiner

*Primary Examiner* — Carl H Layno
*Assistant Examiner* — Eugene Wu
(74) *Attorney, Agent, or Firm* — Michael C. Soldner

(57) ABSTRACT

Systems and techniques that enable a user to selectively extend the time prior to providing an indication of power source depletion, e.g., allow an extended the recommended replacement time (RRT) prior to providing an elective replacement indication (ERI), are described. The user provides input, which may indicate an acceptable level of implantable medical device performance, e.g., that lesser performance for a period between a default RRT and an extended RRT is acceptable. In response to the input, the time until providing an RRT/ERI notification, or some other indication of depletion of the implantable medical device power source, may be extended.

11 Claims, 6 Drawing Sheets

RECOMMENDED REPLACEMENT TIME BASED ON USER SELECTION

TECHNICAL FIELD

The invention relates to the provision of information regarding power source depletion and, more particularly, to the provision of information regarding the depletion of power sources in implantable medical devices.

BACKGROUND

As a chemical reaction driven power source, such as a battery, is used, the reactants within the power source are consumed. Over time, the performance of the power source decreases, and the power source will eventually need to be recharged or replaced. For many surgically implanted medical devices, replacement of a drained power source may expose a person to risks associated with surgery. For example, to replace a power source in a pacemaker or similar implanted device, the device containing the power source often needs to be surgically removed, and a new device with a new power source inserted.

In general, despite surgical risks, it is desired to replace an implanted medical device in advance of significant depletion of its power source. More particularly, it is generally desired to replace an implanted medical device in advance of changes in device performance due to depletion of the power source. Implanted medical devices often provide a warning or other notification to the patient and/or a clinician so that a surgical procedure to replace the implanted device may be scheduled and completed in advance of changes in device performance due to depletion of the device power source. The warning or notification is sometimes referred to as, or provided via, an elective replacement indicator (ERI). The time at which such warnings or other notification are provided has sometimes been referred to as the recommended replacement time (RRT).

In general, implanted medical devices provide such warnings or indications of power source depletion upon the occurrence of a predetermined condition. More particularly, implanted medical devices generally monitor one or more parameters of the power source or the implanted medical device, such as battery voltage or impedance, and compare values of the parameters to one or more predetermined thresholds to determine when to provide the warning or indication of power source depletion. The threshold is typically a predetermined value that is common for every implanted medical device of a particular model, and selected such that the indication or warning is provided early enough to avoid degradation of device performance due to power source depletion in most circumstances, e.g., for most rates of power source depletion.

SUMMARY

In general, the disclosure describes systems and techniques that enable a user to selectively extend the time prior to providing an indication of power source depletion, e.g., allow an extended the RRT prior to providing an ERI. The user provides input, which may indicate an acceptable level of implantable medical device performance, e.g., that lesser performance for a period between a default RRT and an extended RRT is acceptable. In some examples, the level of performance of the IMD may refer to a length of time for charging a discharge capacitor prior to providing a relatively high voltage therapy, such as defibrillation. In response to the input, the time until providing an RRT/ERI notification, or some other indication of depletion of the implantable medical device power source, may be extended. Patients who may be able to tolerate the decreased performance of the implantable medical device during the period between a default and extended ERI, may benefit from delaying the ERI/RRT notification, and thus delaying surgery to replace the implantable medical device.

In one example, an implantable medical device system comprises an implantable medical device comprising a power source, wherein at least one performance characteristic of the implantable medical device changes as the power source is consumed over time. The system further comprising a processor configured to receive user input indicating an acceptable level of performance of the implantable medical device with respect to the performance characteristic of the implantable medical device, and determine a time for providing an indication regarding depletion of the power source to the user based on the user input.

In another example, a method comprises receiving, by a processor, user input indicating an acceptable level of performance of an implantable medical device with respect to a performance characteristic of the implantable medical device, wherein the performance characteristic of the implantable medical device changes as a power source of the implantable medical device is consumed over time, and determining, by the processor, a time for providing an indication regarding depletion of the power source to the user based on the user input.

In another example, a computer-readable storage medium comprises instructions that cause a programmable processor to receive user input indicating an acceptable level of performance of an implantable medical device with respect to a performance characteristic of the implantable medical device, wherein the performance characteristic of the implantable medical device changes as a power source of the implantable medical device is consumed over time; and determine a time for providing an indication regarding depletion of the power source to the user based on the user input.

The details of one or more examples are set forth in the accompanying drawings and the description below. Other features, objects, and advantages will be apparent from the description and drawings, and from the claims.

DETAILED DESCRIPTION

Figure 1:
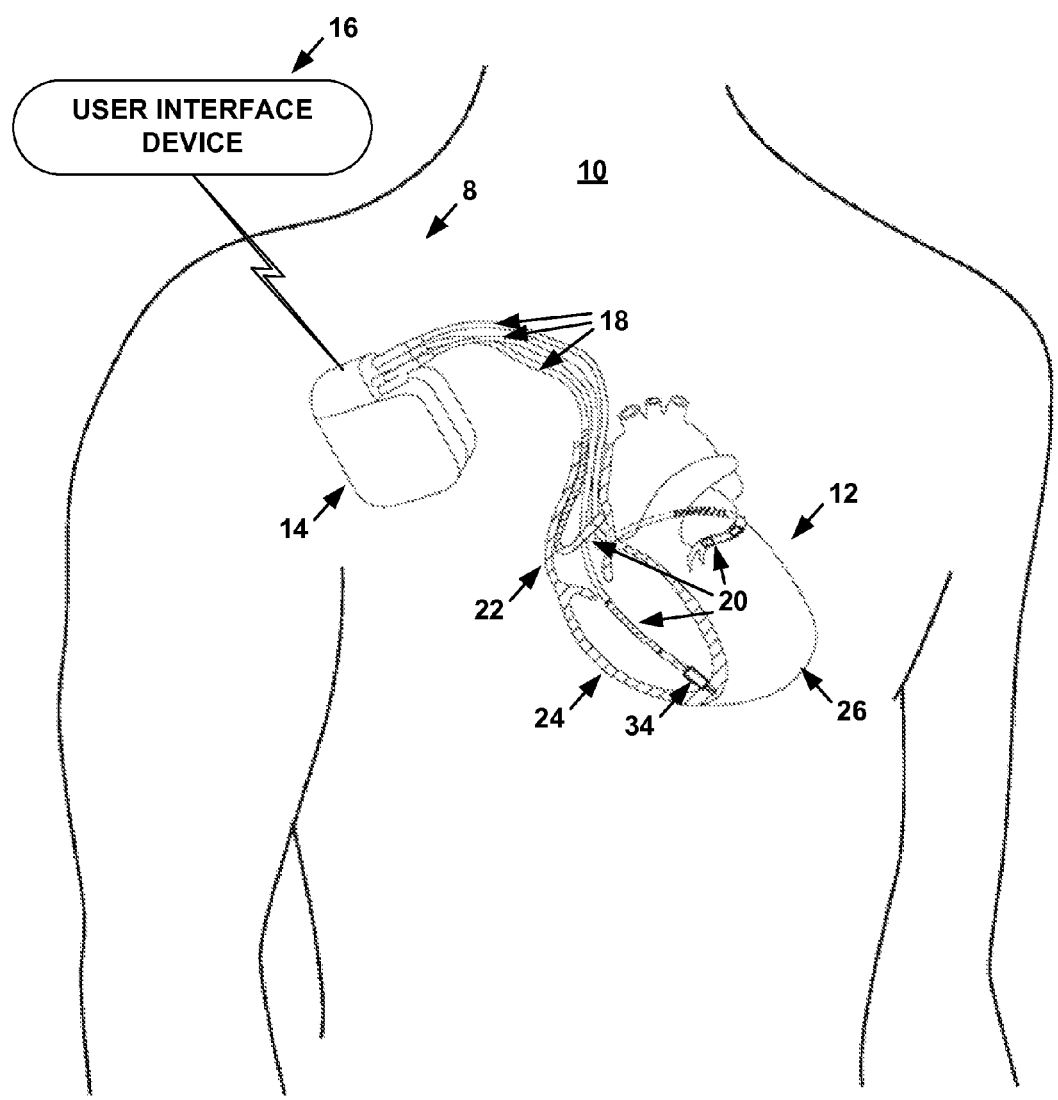
FIG. 1 is a conceptual diagram depicting an example system that includes an implantable medical device implanted within a patient and an external user interface device for interacting with the implantable medical device.

FIG. 1 is a conceptual diagram illustrating a system 8 that includes an implantable medical device (IMD) 14 implanted within a patient 10. As illustrated in FIG. 1, system 8 may also include an external user interface device 16, e.g., a programmer or other computing device, for interacting with the IMD. For purposes of example, IMD 14 is depicted and described throughout this disclosure as an implantable pacemaker, cardioverter-defibrillator, or pacemaker-cardioverter-defibrillator. However, the techniques of this disclosure are not limited to implementation in such devices, or systems including such devices. IMD 14 may include any kind of implantable medical device including a power source, and the techniques described herein with respect to implantable pacemakers, cardioverter-defibrillators, and pacemaker-cardioverter-defibrillators are adaptable to other kinds of implantable medical devices including power sources, as would be readily apparent to a person having ordinary skill in the art.

IMD 14 is powered by a power source, e.g., power source 42 (FIG. 2), that has an output (e.g., voltage output) which decays as the power source is used. In some examples, the power source may have varying decay characteristics as the power source achieves different depths of discharge, e.g., depending on the fraction of the total capacity of the power source discharged. After significant depletion of the power source, the performance of certain functions by the IMD, such as delivery of therapy, patient monitoring, or communication, may be impaired. IMD 14 and/or user interface device 16 are configured to monitor the discharge level of the power source and/or a level of performance of one or more functions of the IMD, and provide a warning or other indication to the patient and/or a clinician, e.g., an ERI at an RRT, so that a surgical procedure to replace the IMD may be scheduled and completed in advance of undesired changes in device performance due to depletion of the device power source. In conventional systems, the threshold power source discharge level or other IMD performance threshold for issuing the ERI/RRT notification is specified by the IMD manufacturer and universal for all patients. Hereinafter, a warning or other notification to the patient and/or a clinician so that a surgical procedure to replace the IMD may be scheduled and completed in advance of changes in device performance due to depletion of the IMD power source is referred to as an ERI/RRT notification, although the techniques described herein are equally applicable to any such notification.

According to the techniques described herein, IMD 14 and/or user interface device 16 may delay provision of an ERI/RRT notification relative to when it would be provided according to default power source or IMD performance thresholds, and thus the usable life of an IMD may be extended, based on user selection of an acceptable performance level of the IMD. In this manner, if the patient is able to tolerate reduced performance of the IMD, issuance of an ERI/RRT notification and replacement of the IMD may be delayed. For example, if a patient is able to tolerate increased charge times prior to delivery of a high voltage therapy, e.g., defibrillation, in response to detection of a tachyarrhythmia by the IMD, a clinician may provide an indication that such reduced performance of the IMD is acceptable via user interface device 16. In response to the user input, IMD 14 and/or user interface device 16 may modify the ERI/RRT. In some examples, in response to the user input, IMD 14 and/or user interface device 16 may modify an IMD performance threshold associated with high voltage therapy charge time, which may in effect delay the provision of the ERI/RRT notification by the IMD or user interface device.

IMD 14 may provide electrical stimulation to heart 12 of patient 10, and sense electrical signals within patient, e.g., associated with the depolarization and repolarization of heart 12, via leads 18 and electrodes 20. Leads 18 connect electrodes 20 to IMD 14. Electrodes 20 may be implanted in or proximate to one or more of the left atrium, right atrium 22, right ventricle 24, or left ventricle 26 of heart 12. In some examples, one or more electrodes may be formed integral with the housing of IMD 14. In some examples, an IMD need not be coupled to leads, and may instead rely on one or more electrodes integral to the housing of IMD 14 for electrical sensing and/or stimulation.

IMD 14 may include one or more communications means, such as a radio antenna, micro-electromechanical system reed switches, or similar devices, to allow a user to interact with IMD 14 through user interface device 16. User interface device 16 may be a hand held programmer or other computing device configured to communicate with, and in some cases, program IMD 14. User interface device 16 may include a visual display or other means of presenting data transmitted from IMD 14 to a user of user interface device 16. User interface device 16 may also include a means, such as a keypad or touch screen, to allow a user to modify one or more parameters of IMD 14, including selecting or otherwise indicating an acceptable performance level for IMD 14, as described in greater detail below. In some examples, user interface device 16 may allow the user opportunities to indicate an acceptable performance level of IMD 14 at multiple times, e.g., at implant, at different depths of discharge of the IMD power source, or when a default RRT for IMD 14 is reached.

Figure 2:
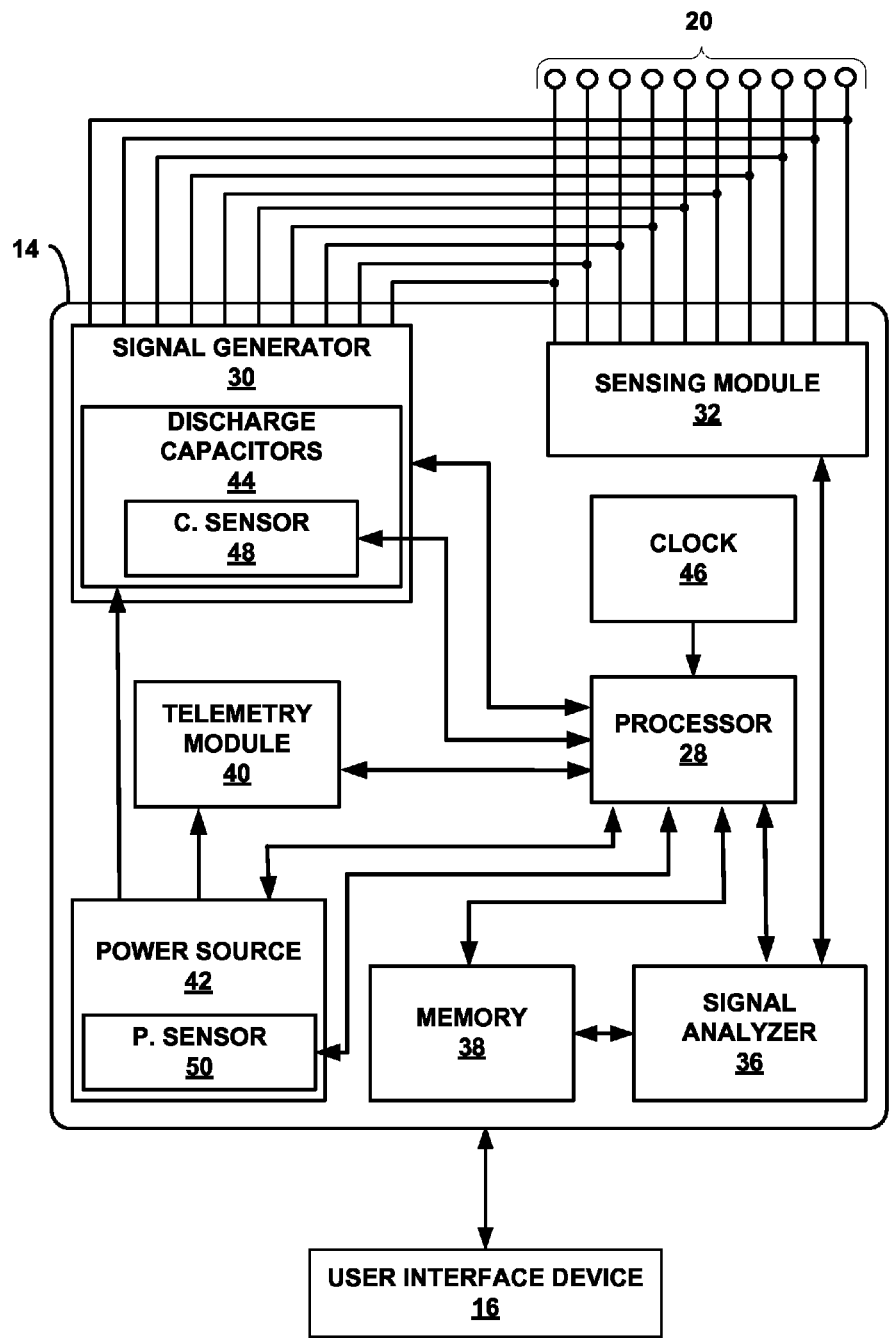
FIG. 2 is a block diagram illustrating an example configuration of the implantable medical device of FIG. 1.

FIG. 2 is a block diagram illustrating an example configuration of IMD 14. As illustrated in FIG. 2, IMD 14 may include a processor 28, signal generator 30, sensing module 32, signal analyzer 36, memory 38, telemetry module 40, power source 42, and clock 46. Signal generator 30 and sensing module 32 may be connected to electrodes 20, e.g., via leads 18. Signal generator 30 may include one or more discharge capacitors 44, e.g., for delivery of therapeutic signal, such as pacing, cardioversion or defibrillation pulses, via electrodes 20. Processor 28 may receive data regarding the performance of power source 42 and/or IMD 14 via one or more sensors, such as a charge sensor 48 monitoring the performance of discharge capacitor 44, or power sensor 50 monitoring one or more parameters of power source 42. IMD 14 may communicate with user interface device 16 via telemetry module 40.

Processor 28 may be programmed or otherwise configured to control the operation of IMD 14. In some examples, processor 28 may perform or control the functions ascribed to IMD 14 or various modules of IMD herein using software instructions stored in memory 38. Processor 28 may include one or more microprocessors, digital signal processors (DSPs), application specific integrated circuits (ASICs), field programmable gate arrays (FPGAs), or any other equivalent integrated or discrete logic circuitry, as well as any combinations of such components.

Sensing module 32 may receive electrical signals representative of cardiac activity via various combinations of two or more electrodes 20, i.e., via various sensing vectors. Through the various sensing vectors, sensing module 32 may receive signals representative of electrical activity of various regions of heart 12 of patient 10, allowing IMD 14 to detect the progression of electrical signals through heart 12. In some examples, sensing module 32 includes circuitry configured to detect and provide indications of the occurrence of specific cardiac events, such as depolarizations, e.g., R-waves and P-waves, based on the signals.

Signal analyzer 36 may receive the electrical signals of heart 12 or other data gathered by sensing module 32, e.g., indications of depolarizations or other cardiac events, and interpret the information to, for example, guide the therapy administered by IMD 14. For example, signal analyzer 36 may identify bradycardia or a tachyarrhythmia based on the data, and processor 28 may responsively control signal generator 30 to deliver one or more therapeutic electrical signals to heart 12 via electrodes 20 in response to the identification. As described above, the delivery of such therapeutic signals may involve charging and discharging of discharge capacitors 44. In various examples, signal analyzer 36 may be embodied as a discrete hardware component of IMD 14, a set of software instructions contained in memory 38 and executed by processor 28, or some combination thereof. Signal analyzer 36 may store the data representative of cardiac activity in memory 38, e.g., for analysis by processor 28 and/or transmission to an external device through telemetry module 40.

Memory 38 may include any volatile or non-volatile media, such as a random access memory (RAM), read only memory (ROM), non-volatile RAM (NVRAM), electrically erasable programmable ROM (EEPROM), flash memory, and the like. Memory 38 may contain instructions that, when executed by processor 28 or other modules of IMD 14, control the operation of IMD 14. The contents of memory 38 may be updated through instructions received via telemetry module 40, e.g., from user interface device 16. Memory 38 may also store data gathered by sensing module 32, signal analyzer 36 and onboard sensors, such as power sensor 50, and charge sensor 48. Data from these sensors may be transmitted to user interface device 16 via telemetry module 40.

Telemetry module 40 may include circuitry for transmitting data indicating the status of IMD 14 and, in some examples, the status or recorded monitoring/treatment history of patient 10 to user interface device 16, as well as receiving instructions or other data from the user interface device. Telemetry module 40 may comprise one or more of a radio transceiver for radio frequency communication, a proximal inductive transceiver, a cellular communications device, magnetic communication device, or a Bluetooth or other peer-to-peer communications mechanism, as examples. In some examples, telemetry module 40 may include multiple communications means, allowing IMD 14 to communicate with a range of devices, or at a range of distances or bandwidths, depending on the situation. Telemetry module 40 may establish a communication with user interface device 16 while patient 10 is in the presence of the clinician or other user of user interface device 16. When patient 10 is at home or elsewhere, telemetry module 40 may update a clinician of cardiac or other events via a cellular, telephonic, or internet network, e.g., via an external interface device (not shown) that is equipped to communicate both with telemetry module 40 and such networks.

Power source 42 may include a battery, capacitor, and/or other energy storage device that stores energy and provides electrical power to IMD 14. As IMD 14 consumes the electrical power supplied by power source 42, the output, e.g., voltage and/or current, provided by power source 42 may decay. Power source 42 may be configured to provide an extended period of relatively constant output until power source 42 nears a designed end of life, marked by a more rapid decline in voltage output. This may occur as, for example, the chemicals composing power source 42 are expended in a chemical reaction generating the electrical output. Some examples of power source 42 may include multiple electrochemical reactions, creating a hybrid power output defined by two or more periods of relatively constant voltage interspersed with more rapid decreases in voltage generated.

Clock 46 may be configured to synchronize the functions of IMD 14. Clock 46 may also, in some examples provide a time basis for a measure or estimate of the historical power consumption by IMD 14, and for providing an ERI/RRT notification, by processor 28. The rate of power consumption by IMD 14 may vary from patient-to-patient depending on, for example, the seriousness of the symptoms of the patient, and thus the amount of monitoring or therapy provided to the patient. In some examples, processor 28 may determine the RRT and provide an ERI/RRT notification based on the measured or estimated consumption of power source 42 over time.

Discharge capacitors 44 may include capacitors configured to provide relatively high voltage therapy (relative to cardiac pacing), such as cardioversion and defibrillation therapy, to patient 10. Such high voltage capacitors may have relatively higher voltage capacity. Furthermore, the time required for power source 42 to charge such capacitors to a level sufficient for such higher voltage therapies may be longer than the time required to charge capacitors for delivery of pacing pulses. As power source 42 is depleted, the time required to charge the high capacity capacitors may measurably increase.

Charge sensor 48 may be configured to facilitate measurement of the capacity of power source 42 based on the time required to charge discharge capacitors 44 to a predetermined level. Discharge capacitor 44 may be charged to a known level, e.g., a therapeutic or sub-therapeutic level, which may occur during delivery of therapy, or when the capacitors will be discharged without delivery of therapy to heart 12. Charge sensor 48 may measure the charge in discharge capacitors 44. Processor 28 may compare the charge measured by charge sensor 48 to a threshold, e.g., associated with a therapeutic or sub-therapeutic level, and also may determine the time to reach the threshold charge using the output of clock 46. The charge time may indicate the output available from power source 42, with longer charge times showing a greater depletion, e.g., depth of discharge, of the power source.

In some examples, processor 28 may control periodic testing of the depth of discharge of power source 42 by charging and discharging, e.g., without delivery of therapy to heart 12, one or more of discharge capacitors 44, and measuring the time to reach the predetermined level of charge, as described above. In such examples, the level to which the capacitors are charged may be less than required for therapy, i.e., sub-therapeutic, and may be a fraction of a therapeutic level or a full charge. By charging discharge capacitor 44 to a lower level in this manner, the energy consumption of the periodic test may be reduced. Charge sensor 48 may include a voltage meter, coulomb meter, or other sensor, that measures an electrical characteristic of the charge of discharge capacitor 44. For example, charge sensor 48 may measure the voltage or current drop across discharge capacitor 44, or a resistor connected to the capacitor.

Power sensor 50 may be integrated with, or connected to, power source 42. Power sensor 50 may measure the depletion of power source 42 by measuring the voltage or current output, impedance, or charge remaining of power source 42, and provide the measurement to processor 28. In some examples, power sensor 50 and/or processor 28 may determine the remaining charge of power source 42 by implementing a coulomb counter to determine or estimate the charge depleted from power source over time based on one or more of the voltage or current output of power source 42 measured by power sensor 50 and the output of clock 46.

Processor 28 may use the measure of the decay of power source 42 to determine a course of action, such as notifying the patient or some other user, e.g., via user interface device 16 or another networked computer, that the RRT of power source 42 has been reached and that replacement of IMD 14 may be scheduled. A safety margin may be incorporated into the threshold depth of discharge or other triggering factor for replacement of power source 42, providing time to make arrangements to have power source 42 replaced before the performance of IMD 14 appreciably degrades.

User interface device 16 may be a remote programming device or other computing device configured to interact with IMD 14. User interface device 16 may display output from one or more sensors or sensing module 32 of IMD 14 stored in memory 38. Telemetry module 40 may transmit the data to user interface device 16. User interface device 16 may also allow a user to adjust the operating parameters of IMD 14, and provide options allowing the user to accept or select a reduced performance of IMD 14 prior to or following a first threshold of depth of decay of power source 42 in exchange for extended usable life of power source 42. User selections and updated operating code may be downloaded from user interface device 16 to IMD 14 via telemetry module 40 and stored in memory 38.

Figure 3:
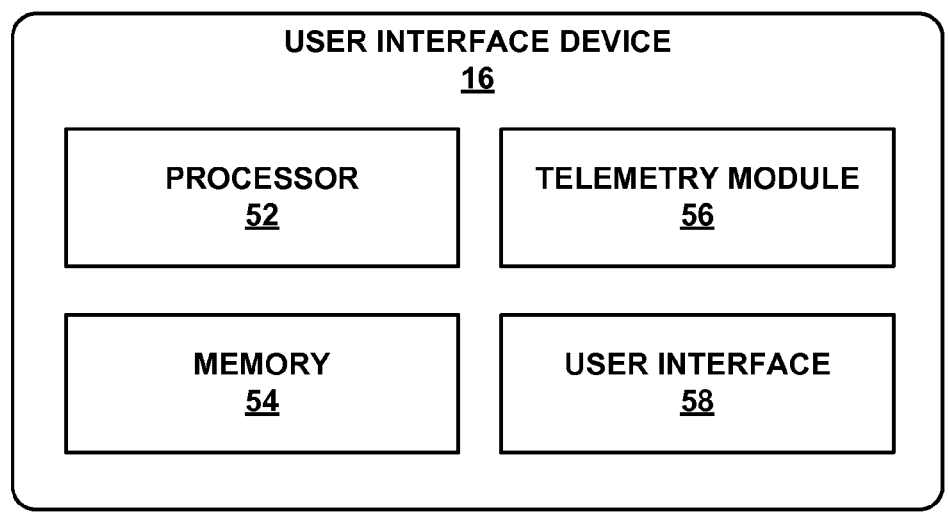
FIG. 3 is a block diagram illustrating an example configuration of the user interface device of FIG. 1.

FIG. 3 is a block diagram illustrating an example configuration of user interface device 16 of FIGS. 1 and 2. As illustrated in FIG. 3, user interface device 16 may include processor 52, memory 54, telemetry module 56, and user interface 58. In general, as indicated above, user interface device 16 may take the form of any type of computing device, such as a handheld, tablet, or desktop computing device.

Processor 52 may receive data regarding the performance of power source 42 or other components of IMD 14 (FIG. 2) from IMD 14, e.g., via telemetry module 40 of IMD 14 (FIG. 2) and telemetry module 56. The data may be generated by one or more sensors, such as a charge sensor 48 or power sensor 50 of IMD 14 (FIG. 2), for example. Processor 52 of user interface device 16 may display such data regarding the performance of power source 42 to patient 10, a clinician, or another user, and may receive commands or other input from the user, via user interface 58. Processor 52 may store the input in memory 54, and transmit one or more parameters or commands responsive to the user input to IMD 14 via telemetry module 56.

Processor 52 may be programmed or otherwise configured to control the operation of user interface device 16. In some examples, processor 52 may perform or control the functions ascribed to user interface device 16 or various modules of user interface device 16 herein using software instructions stored in memory 54. Processor 52 may include one or more microprocessors, digital signal processors (DSPs), application specific integrated circuits (ASICs), field programmable gate arrays (FPGAs), or any other equivalent integrated or discrete logic circuitry, as well as any combinations of such components.

Memory 54 may include any volatile or non-volatile media, such as a random access memory (RAM), read only memory (ROM), non-volatile RAM (NVRAM), electrically erasable programmable ROM (EEPROM), flash memory, and the like. Memory 54 may contain instructions that, when executed by processor 52 or other modules of user interface device 16, control the operation of user interface device 16 and, in some examples, IMD 14. The contents of memory 54 may be updated through instructions received via user interface, 58. Memory 54 may also store data gathered by sensing module 32, signal analyzer 36 and sensors, such as power sensor 50 and charge sensor 48, of IMD 14, which may be received by user interface device 16 from IMD 14 via telemetry module 56.

Telemetry module 56 may include one or more means of receiving data indicating the status of IMD 14 and, in some examples, transmitting instructions or other data to IMD 14. Telemetry module 56 may comprise one or more of a radio transceiver radio frequency communication, a proximal inductive transceiver, a cellular communications device, magnetic communication device, or a Bluetooth or other peer-to-peer communications mechanism, as examples. In some examples, telemetry module 56 may include multiple communications means, allowing telemetry module 56 to communicate with a range of devices, or at a range of distances or bandwidths, depending on the situation. Telemetry module 56 may establish a communication with IMD 14 while patient 10 is in the presence of the clinician or other user of user interface device 16. When patient 10 is at home or elsewhere, telemetry module 56 may receive updates of cardiac or other events from IMD 14, e.g., via a cellular, telephonic, or internet network.

User interface 58 may be configured to allow patient 10 or a clinician to receive data from IMD 14 and input parameters and/or commands to be transmitted to IMD 14. User interface 58 may include elements for visual and, in some examples, audio output, e.g., a display and speakers. User interface 58 may receive input, e.g., via a touch sensitive screen, keyboard, mouse or other pointing device, or any similar devices. Processor 52 may store detected inputs in memory 54, and provide data representing the inputs to IMD 14 via telemetry module 56.

User interface device 16 may provide a user interface for aspects of the various example methods described herein. In some examples, user interface device 16, e.g., processor 52 via user interface 58, may present IMD performance information to a user, prompt a user for input regarding an acceptable level of performance of the IMD, and receive such user input, as described herein. In some examples, user interface 16, e.g., processor 52, may perform any of the methods described herein, including determining an RRT and providing an ERI/RRT, or any other function ascribed to IMD 14, e.g., processor 28. In some examples, IMD 14 and user interface device 16, e.g., their processors, may cooperate to perform the methods described herein. Any portion, or all, of the methods described herein may be performed by either device.

Figure 4:
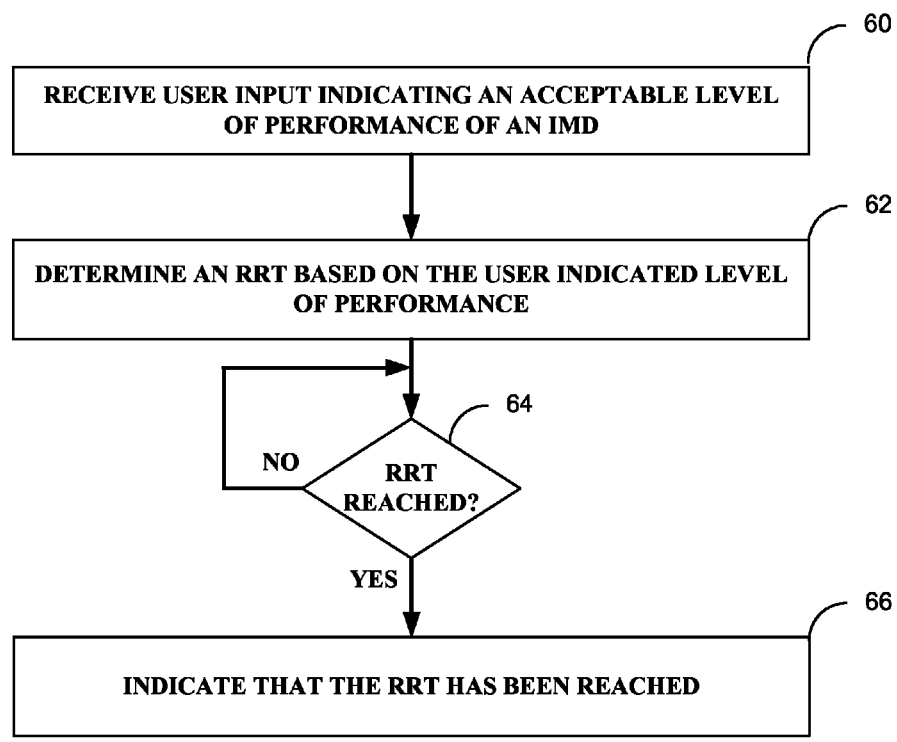
FIG. 4 is a flowchart illustrating an example method for determining when to provide an indication of implantable medical device power source depletion based on user input.
Figure 5:
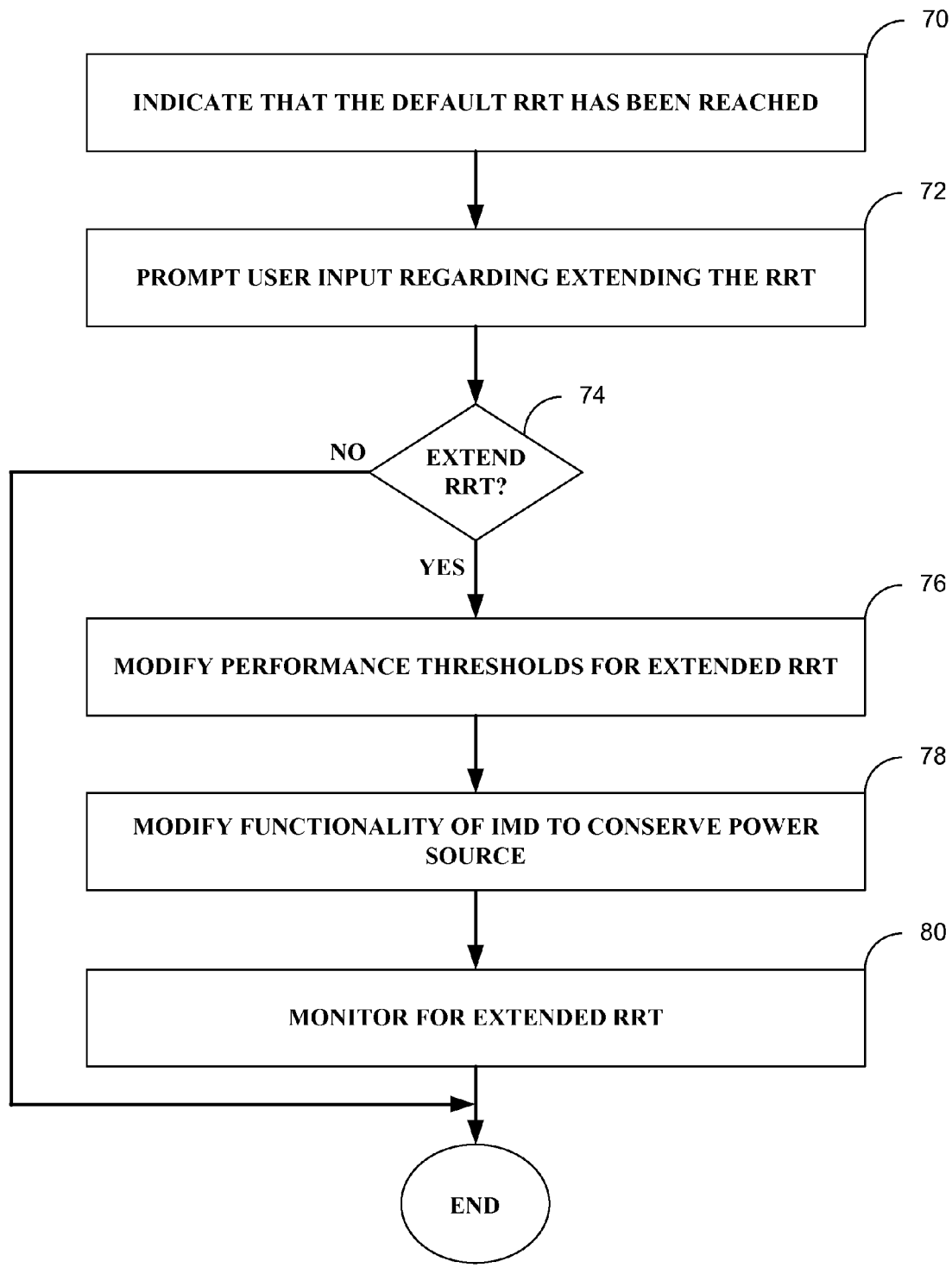
FIG. 5 is a flowchart illustrating an example method for extending the recommended replacement time of an implantable medical device power source.

FIGS. 4 and 5 are flowcharts that illustrate example methods for determining when to provide an ERI/RRT notification based on user input regarding an acceptable level of performance of an IMD according to this disclosure. In some examples, an extended RRT, relative to a default RRT, is determined based on the user input. The example methods, and any part thereof, may be performed by any one or more of the devices described herein, such as one or both of IMD 14 or user interface device 16. For example, the methods described herein may be generally performed by IMD 14, which IMD 14 communicating with the user via user interface device 16. In other examples, user interface device 16 may receive various data from IMD 14, receive user input from a user, determine an RRT, and configure IMD 14 accordingly. FIGS. 4 and 5 are described with respect to examples in which IMD 14 generally performs the example methods.

FIG. 4 is a flowchart illustrating an example method for determining when to provide an indication of IMD power source depletion, e.g., when to indicate that the RRT has occurred, based on user input. According to the example method of FIG. 4, IMD 14 receives user input, e.g., via user interface device 16, that indicates an acceptable level of performance of the IMD with respect to at least one performance characteristic of the IMD (60). IMD 14 determines an RRT based on the user indicated level of performance (62). IMD 14 then determines, e.g., periodically checks, whether the RRT has been reached (64). When the RRT is reached ("YES" branch of 64), IMD indicates to one or more users that the RRT has been reached, e.g., provides an ERI (66). As discussed above, in response to the ERI/RRT indication, the user(s) may schedule a procedure to replace IMD 14.

In some examples, user interface device 16 may display a prompt or other notification to a user of IMD 14. In response to the prompt, the user may provide the input that indicates the acceptable level of IMD performance. In some examples, the prompt may request entry of an acceptable level of performance of at least one performance characteristic, e.g., entry or selection of a numerical value related to IMD performance, such as a high voltage therapy charge time. In other examples, requesting entry of an acceptable level of performance may include presenting a user, via user interface device 16, an option to select an extended RRT along with information regarding the level of performance of one or more characteristics of IMD 14 between the nominal RRT and the extended RRT. Performance characteristics may include, but are not limited to, the charge time of a high voltage therapy discharge capacitor, voltage output of a power source, maximum pacing rate, maximum pacing intensity (e.g., the voltage or current of a pacing pulse), as examples.

The user input regarding an acceptable level of performance may be received at implantation of IMD 14, or later during the operation of IMD 14. A later time of selection may allow a user to better determine whether patient 10 will tolerate any changes to IMD performance attendant with the extended RRT. The acceptable level of performance of IMD 14 and other operating parameters may be stored in memory 38, accessible to processor 28.

Processor 28 of IMD 14 may determine an RRT as a function of the user indicated level of performance (62). In some examples, the processor may determine a duration of time or a particular date/time as the RRT based on the user indicated level of performance. If the user indicates that a lower level of IMD performance will be acceptable for the patient, the time may be longer or later, i.e., the RRT may occur later, than if the user had indicated that lower IMD performance was not acceptable. In such examples, processor 28 of IMD 14 may determine that the RRT has been reached (64) based on a comparison of the output of clock 46 to the determined RRT, which may have been stored in memory 38. The time threshold may indicate a predicated time when the performance of IMD 14 may fall below an acceptable level and may be predicted based on historical use of IMD 14 by patient 10, other patients, a theoretical patient, or a worst-case scenario patient or IMD use pattern.

In some examples, the processor may determine a threshold level for one or more performance characteristics of IMD 14, e.g., of power source 42 or other IMD performance characteristics, based on the user indicated level of performance. The user may indicate threshold values, e.g., numerical values. In other examples, the user may indicate generally that a later RRT is desired and lower performance is acceptable, in response to which the processor may select the threshold level(s). Example performance metrics include a voltage or current output of the power source, a resistance of the power source, or a charge time for a high voltage therapy discharge capacitor. The determined threshold level(s) may be stored in memory 38.

In such examples, to determine whether the RRT has been reached (64), processor 28 may be configured to monitor the one or more performance characteristics through sensors included in IMD 14, such as charge sensor 48 and power sensor 50. Based on a comparison of the output of the sensors to the threshold, processor 28 (or user interface device 16) may determine when the RRT has been reached, e.g., when power source 42 and IMD 14 will no longer meet the user-selected level of performance. Based on the indicated acceptable level of performance, processor 28 of IMD 14 may be able to determine when the determined RRT, e.g., the extended RRT, has been reached, allowing IMD 14 to notify patient 10 or some other user that replacement of IMD 14 is required.

One example of a performance metric is the time required to charge a discharge capacitor for delivery of a high voltage therapeutic shock, e.g., defibrillation shock, to the patient, which may be measured using capacitor sensor 48 and clock 46 as described herein. In some examples, the user input regarding an acceptable level of IMD performance may be with respect to charge time. For example, a prompt to select an acceptable level of performance may indicate that the discharge capacitor charge time will be at least X seconds until the default or currently-programmed RRT is reached, but, if the user desires a later RRT, may be as long as X+a seconds. In other examples, the user may select a value of the discharge capacitor charge time. In some examples, processor 28 may monitor the discharge capacitor charge time, and indicate when the RRT has been reached based on the discharge capacitor charge time, e.g., when the charge time is X seconds, or X+a seconds. In other examples, processor 28 may determine a date/time for the RRT, or a battery voltage or current output for the RRT, based on a user-indicated acceptable level of discharge capacitor charge time.

FIG. 5 is a flowchart illustrating an example method for extending the recommended replacement time of an implantable medical device power source. According to the example method of FIG. 5, user interface device 16 or IMD 14 may indicate that the default or current RRT been reached (70). IMD 14 may transmit a signal via telemetry module 40 to user interface device 16 or other monitoring equipment notifying patient 10 or a clinician that the RRT of IMD 14 has been reached. User interface device 16 may indicate that the recommended replacement time has been reached by displaying a visual alert, sounding an audible alert, or transmitting a message to a device monitored by the clinician or patient, e.g., sending an email message to the email account of the clinician and/or patient. In some examples, IMD 14 may provide a vibratory or other alert instead of or in addition to providing an alert via the user interface or some other external computing device. As discussed above, determination that the RRT has been reached may be made when a determined time has been reached, or when, for example, one or more capacitors of IMD 14 are no longer able to charge within a given time threshold, when power source 42 output voltage or current falls below a set threshold, when the impedance of power source 42 rises above a threshold, usage time and history indicates replacement is warranted, and similar factors.

Upon or after indicating that the default RRT has been reached, user interface device 16 may prompt a user for input regarding extending the RRT (72). As described above, the prompt may include information concerning performance of IMD 14 between the default or current RRT and one or more extended RRT options. For example, the prompt may include information about increased charge times for delivery of high voltage therapy between the current RRT and an extended RRT. The prompt may also indicate other changes that may be made to the performance of IMD 14 during the extended RRT period, such as limiting telemetric communication, as described in greater detail below.

User interface device 16 may receive user input indicate whether to extend the RRT (74). The decision as to whether to extend the RRT may be based on how much therapy patient 10 is using, how well patient 10 may tolerate reduced levels of or promptness of therapy, and the risks associated with replacing IMD 14. In some examples, the health of patient 10 may not be affected by increasing the charging time of discharge capacitors 44, as one example, allowing IMD 14 to function with the reduced capabilities of power source 42. In such a situation, extending the usable life of IMD 14 and postponing surgery may outweigh the effects of reducing the performance of IMD 14 for patient 10. Furthermore, as described below, extending the RRT may, in some examples, involve other modifications to the therapy or monitoring provided by IMD 14, or other functionality of the IMD, and the decision may also be based on whether the patient will tolerate such other changes to IMD performance.

If an extended RRT is accepted or selected, processor 28 of IMD 14 may modify the RRT, which in some examples may include modifying one or more of the IMD performance thresholds for the extended RRT (76). As discussed above, the performance thresholds may include high voltage therapy capacitor charge time, battery voltage or current, or battery resistance. Processor 28 may also modify functionality of IMD 14 to conserve power source 42 to the extent possible during the period between the RRT and extended RRT (78). Processor 28 may then monitor for the occurrence of the extended RRT using any of the techniques described herein, such as those described above with respect to determining whether the RRT is reached (64, FIG. 4) in the example method of FIG. 4 (80).

Modification of the functionality of IMD 14 (78) may include deactivation certain features of IMD 14, such as features that are not required to provide adequate therapy to patient 10. For example, radio-frequency (RF) transceivers built into telemetry module 40 may consume significant amounts of power. While convenient, RF communication may be redundant with magnetic based communication included with IMD 14. By deactivating the RF transceiver in telemetry module 40, IMD 14 may reduce power consumption and extend the life of power source 42.

As another example, processor 28 may impose a maximum cardiac pacing amplitude (voltage or current) or rate during the period between the default RRT and an extended RRT. Were pacing allowed exceed these maximums during the RRT extension period, assumptions regarding other aspects of the performance of IMD 14 during this period may not hold true. For example, were pacing allowed exceed these maximums during the RRT extension period, high voltage therapy charge times may exceed the length considered acceptable when the extended RRT was accepted by the user.

Figure 6:
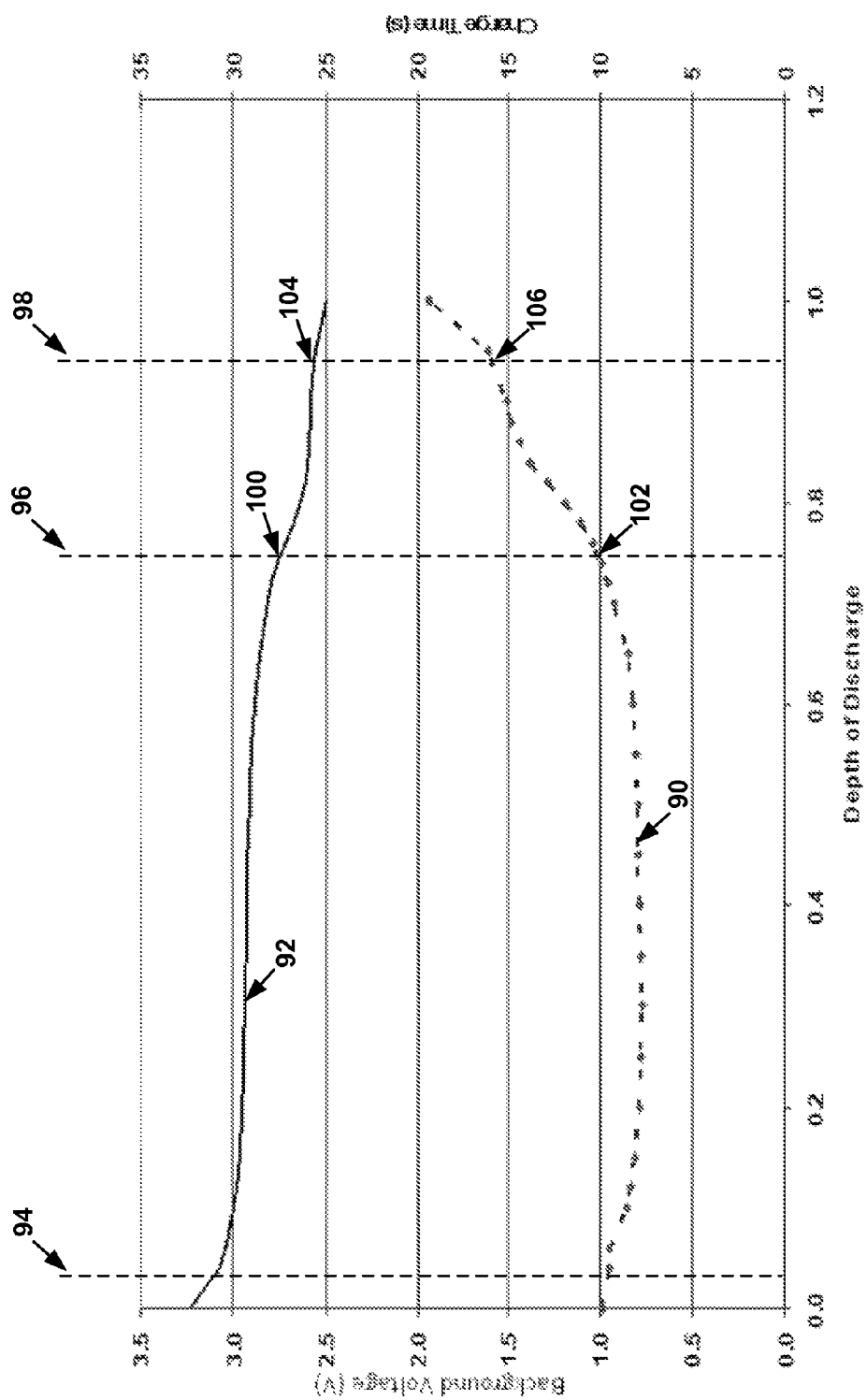
FIG. 6 is a graph illustrating the voltage output of an example power source and corresponding charge times for charging a capacitor of an implantable medical device equipped with the power source over a depletion history of the power source.

FIG. 6 is a graph illustrating the voltage output of an example power source and corresponding charge times for charging a therapy capacitor of an IMD equipped with the power source over a depletion history of the power source. Curve 90 represents the charging time of a discharge capacitor of the IMD. Curve 92 represents the voltage output of a power source of the IMD. The x-axis of the figure displays depth of discharge (DOD), the fraction of the energy of the power source consumed, and represents the life span of the power source elapsed since the installation of the power source in the IMD.

Implantation of the IMD occurs at DOD mark 94. The power source of the IMD may be discharged slightly before implanting due to leakage and decay during storage as well as various preparatory activities, such as programming the IMD, before implantation. At implantation, the power source may provide an output of approximately 3.1 to 3.2 volts and allow the discharge capacitor to charge in approximately 10 seconds. Immediately following implantation, the power source experiences an abrupt but relatively small decline in potential output followed by an extended period of relatively constant output capacity with only a gradual decline. This corresponds with gradual increase in charge times of the discharge capacitor.

As the DOD approaches 60 to 70 percent, the rate of voltage and power decay of the power source increases. In a typical power source the increase in the rate of decay of the power source may be expected to continue until the power source is completely discharged. The electrochemistry of the power source may be adjusted to alter the trajectory of the decay of the power source, attempting to maintain the highest output for as long as possible followed by an abrupt failure or to maintain a more moderate output with a moderate decay rate. The transition into increased rates of decay may mark a recommended replacement point, set, for example, by a threshold DOD that leaves sufficient performance in the power source to safely operate the IMD for a period of time to allow the patient using the device to get the power source replaced. As the available output capacity of the power source decreases, the charging time for the discharge capacitor corresponding increases.

Between DOD mark 96 and DOD mark 98 the acceleration of the decay of the power source decreases. This occurs when the power source is a hybrid, e.g., a power source formed by including multiple electrochemical reactions that provide a plurality of temporary regions of stable output, albeit at a reduced levels, near the complete discharge of the power source. This second region of stable output may allow the usable life of the power source to be extended, provided the patient is able tolerate the reduced performance of the IMD. Curve 90 shows the increase in charging time, rising from 10 seconds to 15 or more seconds, that occurs because of the reduced power output of the power source. The rate of increase of the charge time shown by curve 90 slows as the DOD of curve 92 levels. By enabling the user of the IMD to choose the acceptable level of performance of the IMD, replacement of the IMD may be delayed for certain patients.

In one example, DOD mark 96 may correspond to a current or default RRT, and DOD mark 98 may correspond to an extended RRT. The voltage 100 on curve 92 may be a threshold value for identification of the RRT, and the voltage 104 may be a threshold value for identification of the extended RRT. Similarly, charge times 102 and 106 on curve 90 may be thresholds for RRT or extended RRT identification, and/or charge time 106 may be provided to a user as information regarding the performance of IMD for the user to indicate an acceptable level of performance of the IMD.

Various examples have been described. These and other examples are within the scope of the disclosure.

The invention claimed is:

1. An implantable medical device system comprising:
an implantable medical device comprising a power source, wherein at least one performance characteristic of the implantable medical device changes as the power source is consumed over time; and
one or more processors configured to:
determine a default time to provide an indication of depletion of the power source based on a default level of performance of the implantable medical device with respect to the performance characteristic of the implantable medical device;
provide a prompt to a user for user input that indicates an acceptable level of performance of the implantable medical device with respect to the performance characteristic of the implantable medical device;
receive the user input, wherein the user input indicates that the acceptable level of performance of the implantable medical device with respect to the performance characteristic is lower than the default level of performance of the implantable medical device with respect to the performance characteristic;

determine an extended time to provide the indication of depletion of the power source based on the user input, wherein the extended time comprises a future time when the performance characteristic of the implantable medical device no longer meets or exceeds the user-indicated acceptable level of performance, and wherein the extended time is later than the default time to provide the indication;

monitor the level of the performance characteristic of the implantable medical device; and provide the indication of depletion of the power source at the extended time, wherein the prompt prompts the user to select the extended time for the one or more processors to provide the indication of depletion of the power source in response to reaching the default time to provide the indication of depletion of the power source.

2. The implantable medical device system of claim 1, wherein the performance characteristic of the implantable medical device comprises a charge time of a discharge capacitor of the implantable medical device.

3. The implantable medical device system of claim 2, wherein the implantable medical device is configured to discharge the discharge capacitor to deliver defibrillation therapy.

4. The implantable medical device system of claim 1, wherein the default time comprises a default recommended replacement time for the implantable medical device and the extended time comprises an extended recommended replacement time for the implantable medical device, wherein the extended recommended replacement time is later than the default recommended replacement time.

5. The implantable medical device system of claim 1, wherein the prompt indicates a future level of performance of the implantable medical device with respect to the performance characteristic.

6. The implantable medical device system of claim 1, wherein the prompt prompts the user to select a level of performance of the implantable medical device with respect to the performance characteristic, and the user input comprises a selected level of performance.

7. The implantable medical device system of claim 1, wherein the implantable medical device comprises at least one processor of the one or more processors.

8. The implantable medical device system of claim 1, further comprising an external user interface device that is configured to communicate with the implantable medical device and comprises at least one processor of the one or more processors.

9. A non-transitory computer-readable storage medium comprising instructions that cause one or more programmable processors to:

determine a default time to provide an indication of depletion of a power source based on a default level of performance of an implantable medical device with respect to a performance characteristic of the implantable medical device, wherein the performance characteristic of the implantable medical device changes as the power source of the implantable medical device is consumed over time;

provide a prompt to a user for user input that indicates an acceptable level of performance of an implantable medical device with respect to a performance characteristic of the implantable medical device;

receive the user input, wherein the user input indicates that the acceptable level of performance of the implantable medical device with respect to the performance characteristic is lower than the default level of performance of the implantable medical device with respect to the performance characteristic;

determine an extended time to provide the indication of depletion of the power source based on the user input, wherein the extended time comprises a future time when the performance characteristic of the implantable medical device no longer meets or exceeds the user-indicated acceptable level of performance, and wherein the extended time is later than the default time to provide the indication;

monitor the level of the performance characteristic of the implantable medical device; and provide the indication of depletion of the power source at the extended time, wherein the prompt prompts the user to select the extended time to provide the indication of depletion of the power source in response to reaching the default time to provide the indication of depletion of the power source.

10. The non-transitory computer-readable storage medium of claim 9, wherein the performance characteristic of the implantable medical device comprises a charge time of a discharge capacitor of the implantable medical device.

11. The non-transitory computer-readable storage medium of claim 9, wherein the prompt prompts the user to select a level of performance of the implantable medical device with respect to the performance characteristic, and the user input comprises a selected level of performance.

* * * * *